United States Patent
Dong et al.

(10) Patent No.: US 11,120,562 B2
(45) Date of Patent: Sep. 14, 2021

(54) POSTURE ESTIMATION METHOD, POSTURE ESTIMATION APPARATUS AND COMPUTER READABLE STORAGE MEDIUM

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventors: Zehua Dong, Beijing (CN); Minglei Chu, Beijing (CN); Lili Chen, Beijing (CN); Hao Zhang, Beijing (CN); Jiankang Sun, Beijing (CN); Yukun Sun, Beijing (CN); Jinghua Miao, Beijing (CN); Zhifu Li, Beijing (CN); Xuefeng Wang, Beijing (CN); Hongzhen Xue, Beijing (CN)

(73) Assignees: BEIJING BOE OPTOELECTRONICS TECHNOLOGY CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 125 days.

(21) Appl. No.: 16/537,241

(22) Filed: Aug. 9, 2019

(65) Prior Publication Data
US 2020/0286245 A1    Sep. 10, 2020

(30) Foreign Application Priority Data
Mar. 7, 2019  (CN) .......................... 201910173038.1

(51) Int. Cl.
*A61B 5/11* (2006.01)
*G01C 21/16* (2006.01)
(Continued)

(52) U.S. Cl.
CPC .......... *G06T 7/277* (2017.01); *G06K 9/00369* (2013.01); *G06T 7/207* (2017.01);
(Continued)

(58) Field of Classification Search
None
See application file for complete search history.

(56) References Cited

U.S. PATENT DOCUMENTS

2017/0003764 A1*  1/2017  Li .......................... G06T 19/006
2020/0039522 A1*  2/2020  Nakaoka ............... B60W 40/10

FOREIGN PATENT DOCUMENTS

| CN | 102955477 A | 3/2013 |
| CN | 103611324 A | 3/2014 |

(Continued)

OTHER PUBLICATIONS

Hu et al., "A Minature, Low-cost MEMS AHRS with Application to Posture Control of Robotic Fish," 2013 IEEE International Instrumentation and Measurement Technology Conference (I2MTC), May 6-9, 2013 (Year: 2013).*

(Continued)

*Primary Examiner* — Soo Shin
(74) *Attorney, Agent, or Firm* — Kinney & Lange, P.A.

(57) ABSTRACT

The present disclosure provides a posture estimation method, a posture estimation apparatus, and a computer readable storage medium. Here, the posture estimation method includes: calculating an angular velocity control amount at a current moment based on a measured acceleration value and an estimated acceleration value at the current moment; correcting the measured angular velocity value at the current moment according to the calculated angular velocity control amount to obtain the corrected angular velocity value at the current moment; and obtaining an estimated posture quaternion value at a next moment accord- (Continued)

ing to the corrected angular velocity value obtained by calculation and an estimated posture quaternion value at the current moment.

14 Claims, 3 Drawing Sheets

(51) Int. Cl.
  *G06F 1/16* (2006.01)
  *G06F 3/01* (2006.01)
  *G06K 9/00* (2006.01)
  *G06T 19/00* (2011.01)
  *G06T 7/207* (2017.01)
  *G06T 7/277* (2017.01)
  *G06T 7/60* (2017.01)
  *G06T 7/73* (2017.01)

(52) U.S. Cl.
  CPC .............. *G06T 7/74* (2017.01); *G06T 19/006* (2013.01); *A61B 5/1116* (2013.01); *A61B 5/1118* (2013.01); *G06F 3/011* (2013.01); *G06T 7/60* (2013.01); *G06T 2207/10028* (2013.01)

(56) References Cited

FOREIGN PATENT DOCUMENTS

| CN | 106249745 A | 12/2016 |
|---|---|---|
| CN | 108827299 A | 11/2018 |
| RU | 2615032 C1 | 4/2017 |

OTHER PUBLICATIONS

Li et al., "Quadrotor Drift Error Correctin Based on Adaptive PID," 2018 Chinese Automation Congress (CAC), Nov. 30-Dec. 2, 2018 (Year: 2018).*

Valenti et al., "Keeping a Good Attitude: A Quaternion-Based Orientation Filter for IMUs and MARGs," Sensors 2015, 15, 19302-19330; doi: 10.3390/s150819302 (Year: 2015).*

Setting of Data Collection Thread and Data Processing Thread of Quadcopter, 2015. 20 pages.

First Chinese Office Action dated May 29, 2020, received for corresponding Chinese Application No. 201910173038.1, 34 pages.

* cited by examiner

POSTURE ESTIMATION METHOD, POSTURE ESTIMATION APPARATUS AND COMPUTER READABLE STORAGE MEDIUM

CROSS-REFERENCE TO RELATED APPLICATION(S)

This application claims priority to the Chinese Patent Application No. 201910173038.1, filed on Mar. 7, 2019, entitled "POSTURE ESTIMATION METHOD, POSTURE ESTIMATION APPARATUS AND COMPUTER READABLE STORAGE MEDIUM", which is incorporated herein by reference in its entirety.

TECHNICAL FIELD

The present disclosure relates to the field of posture estimation technology, and more particularly, to a posture estimation method and apparatus, and a computer readable storage medium.

BACKGROUND

In many application scenarios, for example, a scenario in which a multi-rotor drone is in a flight process, a scenario in which a satellite is in an emission process, a scenario in which a missile is in a navigation process, as well as in the Virtual Reality (VR) technology which has emerged in recent years, it is necessary to estimate a posture of a certain three-dimensional target object. When the posture of the three-dimensional target object is estimated, the posture of the three-dimensional target object is usually estimated and calculated according to corresponding measurement data acquired by sensors such as an accelerometer, a magnetometer, and a gyroscope etc.

In the related art, the commonly-used posture estimation methods comprise an extended Kalman filtering method, a complementary filtering method, a gradient descent method, etc. However, the above-mentioned related posture estimation methods have low accuracy in posture estimation for various reasons. For example, the extended Kalman filtering method and the gradient descent method have a large amount of computation when performing the posture estimation, which results in a delay in the posture estimation and a low frequency of the posture estimation, thereby causing a decrease in the accuracy of the posture estimation; and the complementary filtering method has low estimation accuracy, thereby resulting in low accuracy of the posture estimation.

SUMMARY

In view of the above problems in the related art, embodiments of the present disclosure provide a posture estimation method and apparatus, and a computer readable storage medium to solve or at least alleviate the problem of low accuracy of the posture estimation in the related art as described above.

In order to achieve the above purpose, the embodiments of the present disclosure adopt the following technical solutions.

Some embodiments of the present disclosure provide a posture estimation method, comprising: calculating an angular velocity control amount at a current moment based on a measured acceleration value and an estimated acceleration value at the current moment; correcting the measured angular velocity value at the current moment according to the calculated angular velocity control amount to obtain the corrected angular velocity value at the current moment; and obtaining an estimated posture quaternion value at a next moment according to the corrected angular velocity value obtained by calculation and an estimated posture quaternion value at the current moment.

Some other embodiments of the present disclosure provide a posture estimation apparatus, comprising: a processor; and a memory having instructions stored thereon, which when executed by the processor, cause the processor to: calculate an angular velocity control amount at a current moment based on a measured acceleration value and an estimated acceleration value at the current moment; correct the measured angular velocity value at the current moment according to the calculated angular velocity control amount to obtain the corrected angular velocity value at the current moment; and obtain an estimated posture quaternion value at a next moment according to the corrected angular velocity value obtained by calculation and an estimated posture quaternion value at the current moment.

Some other embodiments of the present disclosure provide a computer readable storage medium having one or more instructions stored thereon, which when executed by the processor, cause the processor to perform one or more steps of the posture estimation method described above.

BRIEF DESCRIPTION OF THE ACCOMPANYING DRAWINGS

In order to more clearly explain the technical solutions according to the embodiments of the present disclosure or in the related art, the accompanying drawings to be used in the description of the embodiments or the related art will be briefly described below. Obviously, the accompanying drawings in the following description are only some embodiments of the present disclosure, and other accompanying drawings may be obtained by those of ordinary skill in the art according to these accompanying drawings without any creative work.

DETAILED DESCRIPTION

As described above, there is a problem that the accuracy is low when the posture of the three-dimensional target object is estimated. It has been found through researches that measurement sensors for performing posture estimation on three-dimensional target objects mainly comprise gyroscopes, accelerometers, and magnetometers etc. Here, the gyroscope may measure an angular velocity of a three-dimensional target object, and perform an integral operation on the measured angular velocity to obtain an estimated posture angle of the three-dimensional target object at a next moment, thereby completing the posture estimation of the three-dimensional target object. A result of the posture estimation based on the gyroscope is relatively accurate in a short time, but since the integral operation is required during the posture estimation by the gyroscope, it may result in a large cumulative error over time even if there is a small measurement deviation, thereby causing an inaccurate result of the posture estimation after a long time.

The accelerometer may measure accelerations of the three-dimensional target object in three axis directions in real time. There is no cumulative error in posture angle of the three-dimensional target object at a current moment which is calculated by the accelerometer, but the posture angle is greatly affected by a change in motion state of the three-dimensional target object. Therefore, there is a large noise in an estimated posture angle of the three-dimensional target object at a next moment which is calculated by the accelerometer, thereby resulting in an inaccurate and unstable result of the posture estimation. In practical posture estimation, the gyroscope and the accelerometer are usually required to be used together.

Based on the above researches, the technical solutions according to the embodiments of the present disclosure will be described below in conjunction with the accompanying drawings in the embodiments of the present disclosure. It is apparent that the embodiments described are only a part of the embodiments of the present disclosure, instead of all the embodiments. All other embodiments obtained by those of ordinary skill in the art based on the embodiments of the present disclosure fall within the protection scope of the present disclosure.

Figure 1:
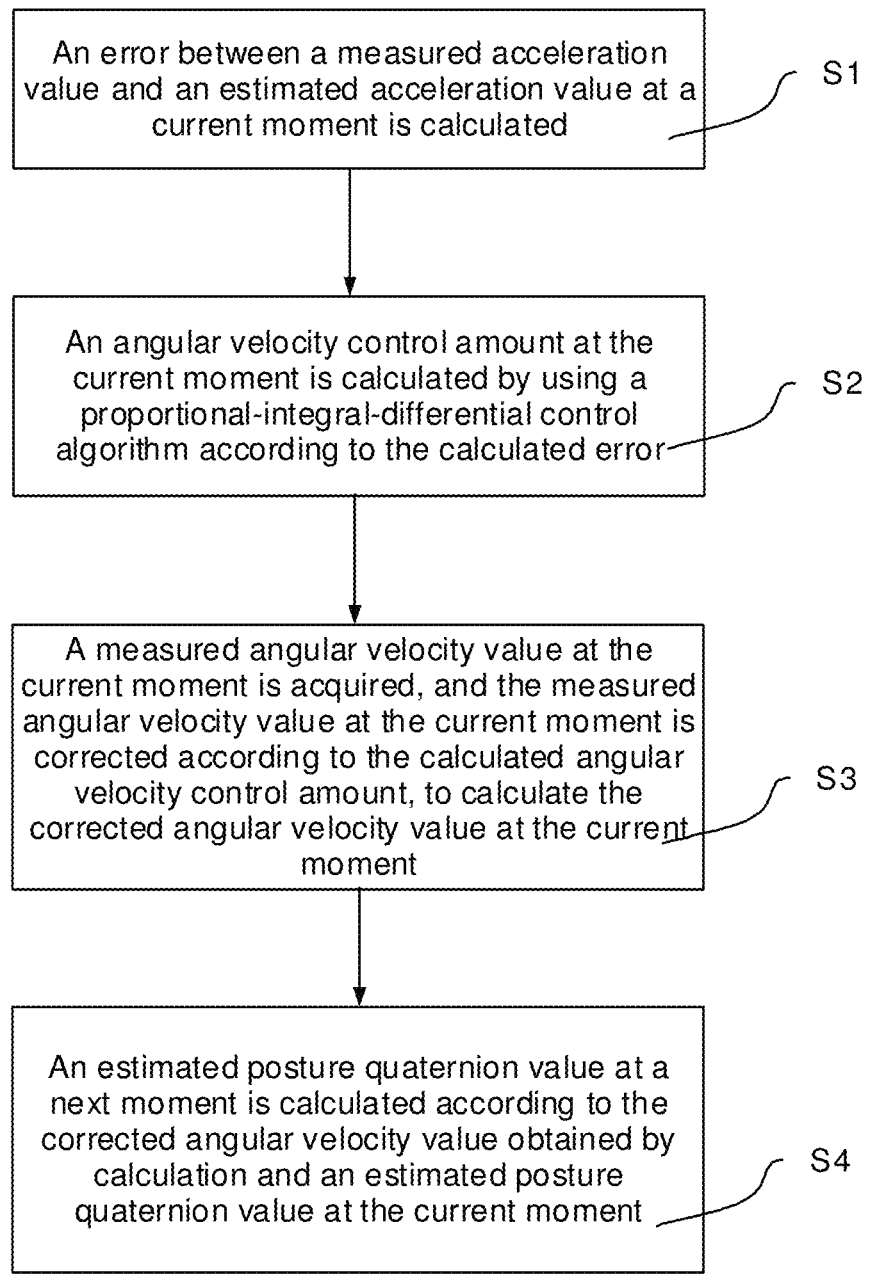
FIG. 1 is a flowchart of an exemplary posture estimation method according to an embodiment of the present disclosure.

The embodiments of the present disclosure provide a posture estimation method, as shown in FIG. 1, comprising the following steps.

In S1, an error between a measured acceleration value and an estimated acceleration value at a current moment is calculated.

In S2, an angular velocity control amount at the current moment is calculated by using a proportional-integral-differential control algorithm according to the calculated error.

In S3, a measured angular velocity value at the current moment is acquired, and the measured angular velocity value at the current moment is corrected according to the calculated angular velocity control amount, to calculate the corrected angular velocity value at the current moment.

In S4, an estimated posture quaternion value at a next moment is calculated according to the corrected angular velocity value obtained by calculation and an estimated posture quaternion value at the current moment.

It should be illustrated that the posture quaternion is usually used to describe posture angle information of the three-dimensional target object, the posture estimation of the three-dimensional target object is estimation of the posture angle of the three-dimensional target object, and completion of calculation of the estimated posture quaternion value of the three-dimensional target object may be regarded as completion of the estimation of the posture angle of the three-dimensional target object, i.e., completion of one posture estimation process.

In step S1 of the posture estimation method described above, the "estimated acceleration value" refers to an acceleration value which is calculated according to the estimated posture angle value at the current moment, wherein the estimated posture angle value refers to an estimated posture angle value which is obtained after integral operation of the angular velocity measured by the gyroscope. The "measured acceleration value" refers to an actual measured acceleration value, which is closer to a true acceleration value. Generally, the measured acceleration value may be approximately regarded as the true acceleration value. Therefore, the error between the measured acceleration value and the estimated acceleration value at the current moment may represent an error between the estimated posture angle value obtained by the gyroscope and the true posture angle value at the current moment.

In the posture estimation method according to the present disclosure, the error between the measured acceleration value and the estimated acceleration value at the current moment is used as an input value, an output value which is calculated by proportional-integral-differential control is used as an angular velocity control amount, and the estimated angular velocity value is corrected according to the angular velocity control amount to achieve correction of a cumulative error caused by integration of the angular velocity. Since the output angular velocity control amount is calculated by the proportional-integral-differential control during the correction of the measured angular velocity value, a steady state error between the measured acceleration value and the estimated acceleration value caused by the proportional control may be eliminated by the integral control on the basis that the error between the measured acceleration value and the estimated acceleration value may be quickly reduced by the proportional control; and a variation trend of the error between the measured acceleration value and the estimated acceleration value in the control process may be predicted by the differential control and overshoot may be prevented from being formed in the control process by the differential control, thereby improving the stability of the output angular velocity control amount. Therefore, after the measured angular velocity value is corrected according to the above angular velocity control amount, the corrected angular velocity value obtained have high accuracy and stability. Therefore, the integral operation is performed according to the corrected angular velocity value, to obtain an estimated posture quaternion value at a next moment which has high accuracy and stability, that is, the accuracy and the stability of the posture estimation are improved.

In addition, since the estimated posture quaternion value is obtained by the above posture estimation method without a large amount of calculation, the posture estimation is performed rapidly, thereby improving the frequency of the posture estimation, reducing the delay in the posture estimation, and further improving the accuracy of the posture estimation.

Figure 2:
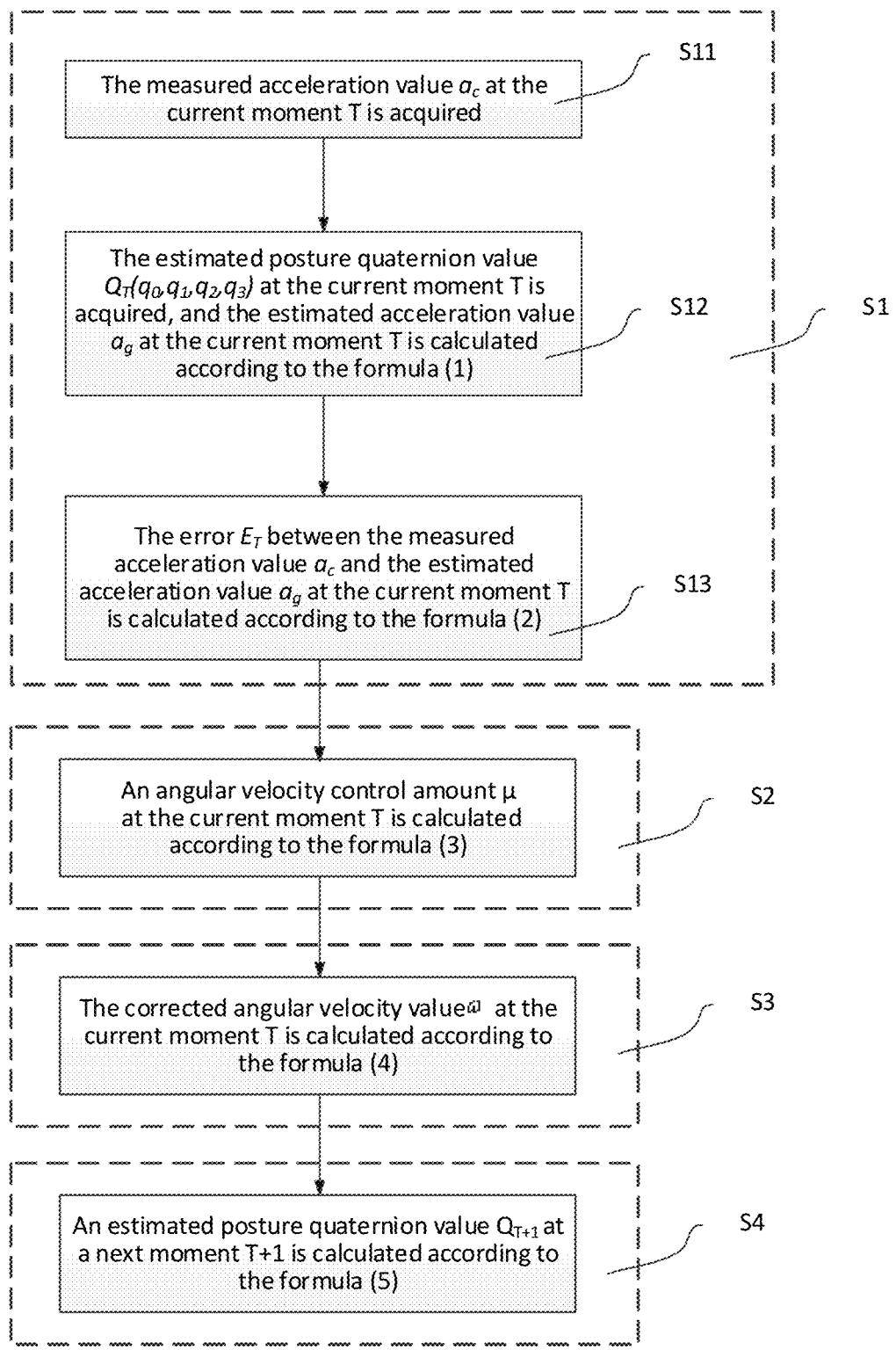
FIG. 2 is a flowchart of an exemplary posture estimation method according to some other embodiments of the present disclosure.

Based on the above technical solution, in some other embodiments according to the present disclosure, as shown in FIG. 2, as a feasible implementation, in step S1 of the above posture estimation method, when the error between the measured acceleration value and the estimated acceleration value at the current moment is calculated, the following steps may be included.

In S11, the measured acceleration value $a_c(x_c,y_c,z_c)$ at the current moment T is acquired.

In S12, the estimated posture quaternion value $Q_T(q_0,q_1,q_2,q_3)$ at the current moment T is acquired, and the estimated acceleration value $a_g$ at the current moment T is calculated according to the following formula (1):

$$a_g = \begin{bmatrix} 2(q_1q_3 - q_0q_2) \\ 2(q_2q_3 + q_0q_1) \\ 1 - 2(q_1^2 + q_2^2) \end{bmatrix}. \quad (1)$$

In S13, the error $E_T$ between the measured acceleration value $a_c$ and the estimated acceleration value $a_g$ at the current moment T is calculated according to the following formula (2):

$$E_T = a_c \otimes a_g = \begin{bmatrix} y_c \cdot [1 - 2(q_1^2 + q_2^2)] - z_c \cdot 2(q_2 q_3 + q_0 q_1) \\ z_c \cdot 2(q_1 q_3 - q_0 q_2) - x_c \cdot [1 - 2(q_1^2 + q_2^2)] \\ x_c \cdot 2(q_2 q_3 + q_0 q_1) - y_c \cdot 2(q_1 q_3 - q_0 q_2) \end{bmatrix}. \quad (2)$$

In step S11, the measured acceleration value $a_c$ may be obtained by a sensor. For example, the measured acceleration value may be measured by an accelerometer, which may accurately acquire an acceleration value of the three-dimensional target object in real time.

As an example, in step S11, the above "estimated posture quaternion value $Q_T(q_0, q_1, q_2, q_3)$ at the current moment T" may be an estimated posture quaternion value which is calculated at a moment T-1 by using the above posture estimation method according to the present disclosure.

It should be illustrated that, in step S12, the above formula (1) may be derived according to the following formulas (6), (7) and (8):

$$a_g = C_n^b \cdot g, \quad (6)$$

$$C_n^b = \begin{pmatrix} 1 - 2(q_2^2 + q_3^2) & 2(q_1 q_2 + q_0 q_3) & 2(q_1 q_3 - q_0 q_2) \\ 2(q_1 q_2 - q_0 q_3) & 1 - 2(q_1^2 + q_3^2) & 2(q_2 q_3 + q_0 q_1) \\ 2(q_1 q_3 + q_0 q_2) & 2(q_2 q_3 - q_0 q_1) & 1 - 2(q_1^2 + q_2^2) \end{pmatrix}, \quad (7)$$

and $$g = \begin{pmatrix} 0 \\ 0 \\ 1 \end{pmatrix}. \quad (8)$$

where the formula (7) is an expression of a direction cosine matrix $C_n^b$ corresponding to the estimated posture quaternion value $Q_T(q_0, q_1, q_2, q_3)$ at the current moment T. The direction cosine matrix Ci is a rotation matrix from a world coordinate system to a coordinate system of the three-dimensional target object, and is used to describe a rotation condition from the world coordinate system to the coordinate system of the three-dimensional target object. When the estimated posture quaternion value $Q_T(q_0, q_1, q_2, q_3)$ of the three-dimensional target object is determined, the direction cosine matrix $C_n^b$ corresponding to the estimated posture quaternion value $Q_T(q_0, q_1, q_2, q_3)$ is also determined. It should also be pointed out that the formula (7) only shows a mathematical expression of the direction cosine matrix $C_n^b$, and the direction cosine matrix $C_n^b$ may be transformed into other expressions after being subjected to mathematical operations.

The formula (8) is an expression of a normalized gravitational acceleration g in the world coordinate system.

In the formula (6), when the normalized gravitational acceleration g in the world coordinate system is transformed into the coordinate system of the three-dimensional target object by the direction cosine matrix $C_n^b$ corresponding to the estimated posture angle value at the current moment, the estimated acceleration value $a_g$ is obtained.

In some embodiments of the present disclosure, as shown in FIG. 2, additionally as a feasible implementation of step S2 of the above posture estimation method, when the angular velocity control amount at the current moment is calculated according to the calculated error by using the proportional-integral-differential control algorithm, the following steps may be included.

The angular velocity control amount μ at the current moment T is calculated according to the following formula (3):

$$\mu = K_p \cdot E_T + K_i \cdot \Sigma_{n=0}^{T} E(n) + K_d \cdot (E_T - E_{T-1}) \quad (3),$$

where $E_{n=0}^{T} E(n)$ represents a discrete integral of an error between a measured acceleration value and an estimated acceleration value from an initial moment 0 to the current moment T; $E_{T-1}$ represents an error between a measured acceleration value and an estimated acceleration value at a last moment T-1; $K_p$ represents a proportional control coefficient; $K_i$ represents an integral control coefficient; and $K_d$ represents a differential control coefficient.

It should be illustrated that in the above posture estimation method, the proportional control coefficient $K_p$ may affect a speed at which the estimated acceleration value $a_g$ converges to the measured acceleration value $a_c$, in the control process. For example, when the proportional control coefficient $K_p$ is large, the estimated acceleration value $a_g$ rapidly converges to the measured acceleration value $a_c$, but large overshoot may easily generated in the control process, which reduces the stability of the control process; and when the proportional control coefficient $K_p$ is small, the estimated acceleration value $a_g$ slowly converges to the measured acceleration value $a_c$.

The integral control factor $K_i$ may affect a speed at which the steady state error is eliminated in the control process. For example, when the integral control coefficient $K_i$ is large, the above steady state error is eliminated rapidly, but a large oscillation is generated in the control process, which reduces the stability of the control process; and when the integral control coefficient $K_i$ is small, the above steady state error is slowly eliminated.

The differential control factor $K_d$ may affect how long the error $E_T$ reaches a stable value in the control process. For example, when the differential control coefficient $K_d$ is large, the error $E_T$ reaches a stable value for a long time, that is, it takes a long time for the adjustment process to reach a stable state; and when the differential control coefficient $K_d$ is small, the differential control has a weak suppression effect on the overshoot, and cannot achieve an effect of suppressing the overshoot from being formed in advance.

As an example, in the above posture estimation method, an execution component which performs the proportional-integral-differential control may be a sensor such as a gyroscope, an accelerometer etc. Here, the proportional control coefficient $K_p$, the integral control coefficient $K_i$, and the differential control coefficient $K_d$ may be determined according to a condition of the execution component which performs the proportional-integral-differential control (for example, a measurement error of the execution component). As an example, the above proportional control coefficient $K_p$, the integral control coefficient $K_i$, and the differential control coefficient $K_d$ may be determined by performing a limited number of experiments on the execution component which performs the proportional-integral-differential control.

It should also be illustrated that the above formula (3) may be obtained according to the following formula (9):

$$\mu_0 = K_p \cdot E_T + K_i \cdot \int_0^t E_T \cdot dt + K_d \cdot \frac{dE_T}{dt}. \quad (9)$$

The formula (9) is a continuous expression of the proportional-integral-differential control algorithm, where $\mu_0$ represents an angular velocity control amount which is not subjected to discrete processing, and t represents a time interval from the initial moment 0 to the current moment T. In practical applications, since the measured acceleration value etc. is acquired at a certain sampling period, that is, there is a certain time interval between two adjacent acquisition processes of measured acceleration values, the error $E_T$ between the measured acceleration value $a_c$ and the estimated acceleration value $a_g$ is also acquired periodically. Therefore, when the angular velocity control amount $\mu$ is calculated by using the proportional-integral-differential control algorithm, a discrete expression of the proportional-integral-differential control algorithm is required to be used. The above formula (3) is the discrete expression of the proportional-integral-differential control algorithm which is obtained by transforming the above formula (9) by performing discrete processing on the above formula (9).

In some embodiments of the present disclosure, as shown in FIG. 2, additionally as a feasible implementation of step S3 of the above posture estimation method, when the corrected angular velocity value at the current moment T is calculated, the following steps may be included:

The corrected angular velocity value $\omega(\omega_x,\omega_y,\omega_z)$ at the current moment T is calculated according to the following formula (4):

$$\omega = \omega_c + \mu \quad (4),$$

where $\omega_c$ represents the measured angular velocity value at the current moment T.

Therefore, the measured angular velocity value at the current moment is corrected by adding the angular velocity control amount and the measured angular velocity value at the current moment T, to obtain the corrected angular velocity value $\omega$ at the current moment T.

In some embodiments of the present disclosure, as shown in FIG. 2, additionally as a feasible implementation of step S4 of the above posture estimation method, when the estimated posture quaternion value at the next moment is calculated, the following steps may be included:

an estimated posture quaternion value $Q_{T+1}(q_0,q_1,q_2,q_3)$ at a next moment T+1 is calculated according to the following formula (5):

$$Q_{T+1}(q_0, q_1, q_2, q_3) = \begin{pmatrix} q_0 \\ q_1 \\ q_2 \\ q_3 \end{pmatrix} + \frac{\Delta T}{2} \begin{pmatrix} -\omega_x \cdot q_1 - \omega_y \cdot q_2 - \omega_z \cdot q_3 \\ +\omega_x \cdot q_0 - \omega_y \cdot q_3 + \omega_z \cdot q_2 \\ +\omega_x \cdot q_3 + \omega_y \cdot q_0 - \omega_z \cdot q_1 \\ -\omega_x \cdot q_2 + \omega_y \cdot q_1 + \omega_z \cdot q_0 \end{pmatrix}, \quad (5)$$

where $\Delta T$ represents a sampling time interval of the measured angular velocity value $\omega_c$.

It should be illustrated that the above formula (5) may be derived according to the following formula (10):

$$Q_{T+1}(q_0,q_1,q_2,q_3) = Q_T(q_0,q_1,q_2,q_3) + \Delta T \cdot \tfrac{1}{2}(\omega \cdot Q_T) \quad (10).$$

When the estimated posture quaternion value $Q_{T+1}(q_0,q_1,q_2,q_3)$ at the next moment T+1 is calculated in the formula (5), the corrected angular velocity value co which is obtained by performing correction using the proportional-integral-differential control is used, and thus the estimated posture quaternion value $Q_{T+1}(q_0,q_1,q_2,q_3)$ at the next moment T+1 which is obtained by using the formula (5) has high accuracy and stability.

It should be illustrated that, a pitch angle and a roll angle in posture angle information of the three-dimensional target object are generally calculated according to an acceleration value. The above embodiments are described by taking the angular velocity control amount being only the pitch angle and the roll angle as an example (that is, the above embodiments are described by taking correction of measured angular velocity values of only the pitch angle and the roll angle as an example).

In some embodiments of the present disclosure, as a feasible implementation of the above posture estimation method, a measured angular velocity value of a yaw angle in the posture angle information may also be corrected. As an example, before the above step S2, the method may further comprise: calculating an error between a measured magnetic field strength value and an estimated magnetic field strength value at the current moment. In step S2, the error according to which the angular velocity control amount at the current moment is calculated by using the proportional-integral-differential control algorithm may further comprise an error between the measured magnetic field strength value and the estimated magnetic field strength value at the current moment. The angular velocity control amount thus obtained comprises not only the angular velocity control amounts of the pitch angle and the roll angle, but also the angular velocity control amount of the yaw angle, thereby further improving the accuracy of the correction of the measured angular velocity value, while improving the accuracy of the posture estimation. As an example, the above measured magnetic field strength value may be obtained by a magnetometer.

It should be illustrated that, in the implementation process, each step of the above posture estimation method may be completed by an integrated logic circuit of hardware in a processor or instructions in a software form. The steps of the method disclosed in connection with the embodiments of the present disclosure may be directly embodied to be implemented by a hardware processor or by a combination of hardware and software modules in a processor. The software modules may be located in a conventional storage medium such as a random access memory, a flash memory, a read only memory, a programmable read only memory, an electrically erasable programmable memory, a register etc. The storage medium may be located in a memory, and a processor may read information in the memory to perform the steps of the above method in combination with the hardware thereof.

Figure 3:
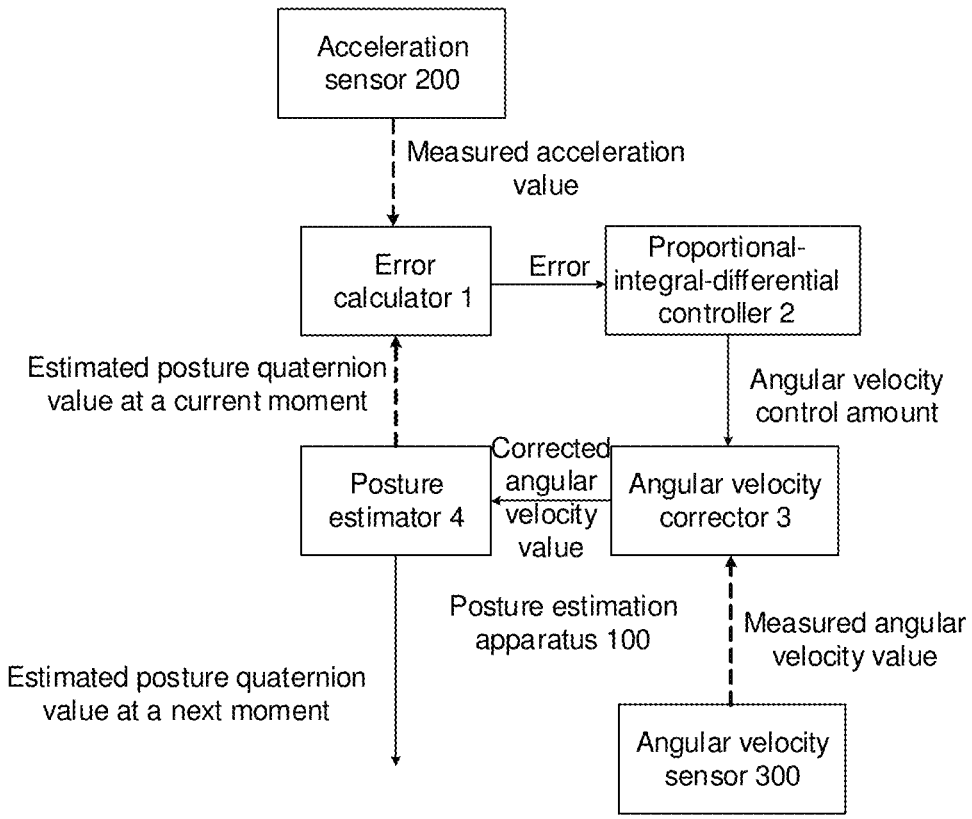
FIG. 3 is a schematic structural diagram of a posture estimation apparatus according to an embodiment of the present disclosure.

In some embodiments of the present disclosure, as shown in FIG. 3, there is also provided a posture estimation apparatus 100, comprising: an error calculator 1 configured to calculate an error between a measured acceleration value and an estimated acceleration value at a current moment; a proportional-integral-differential controller 2 connected to the error calculator 1 and configured to calculate an angular velocity control amount at the current moment by using a proportional-integral-differential control algorithm according to the error calculated by the error calculator 1; an angular velocity corrector 3 connected to the proportional-integral-differential controller 2 and configured to acquire a measured angular velocity value at the current moment, and correct the measured angular velocity value at the current moment according to the angular velocity control amount calculated by the proportional-integral-differential controller 2, to calculate the corrected angular velocity value at the current moment; and a posture estimator 4 connected to the angular velocity corrector 3 and configured to calculate an estimated posture quaternion value at a next moment according to an estimated posture quaternion value at the current moment and the corrected angular velocity value calculated by the angular velocity corrector 3.

The posture estimation apparatus 100 has the same beneficial effects as those of the above posture estimation method, and will not be described in detail here.

In some embodiments, as a possible design, when the error calculator 1 calculates the error between the measured acceleration value and the estimated acceleration value at the current moment, the estimated posture quaternion value at the current moment may be obtained from the posture estimator 4, and the estimated acceleration value at the current moment may be calculated according to the estimated posture quaternion value at the current moment.

In some embodiments, the error calculator 1 may acquire the measured acceleration value from the acceleration sensor 200, and the angular velocity corrector 3 may acquire the measured angular velocity value from the angular velocity sensor 300.

In some embodiments of the present disclosure, there is also provided a computer readable storage medium having stored thereon one or more instructions to perform one or more steps of the above posture estimation method.

The computer readable storage medium has the same beneficial effects as those of the above posture estimation method, and will not be described in detail here.

Figure 4:
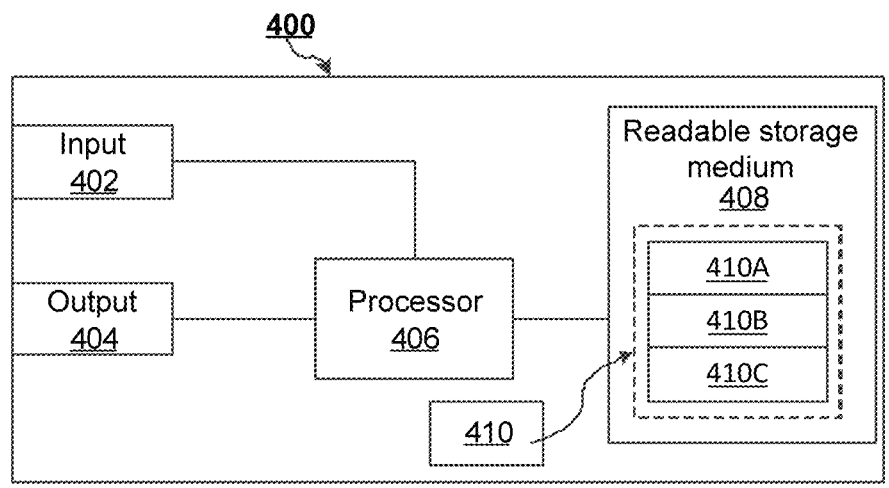
FIG. 4 is a hardware layout diagram of a posture estimation apparatus according to some other embodiments of the present disclosure.

FIG. 4 is a schematic diagram of a hardware arrangement 400 of a posture estimation apparatus according to an embodiment of the present disclosure. The hardware arrangement 400 comprises a processor 406 (for example, a Digital Signal Processor (DSP), a Central Processing Unit (CPU), etc.) The processor 406 may be a single processing unit or a plurality of processing units for performing different actions of a flow of the method described herein. The arrangement 400 may further comprise an input unit 402 for receiving signals from other entities, and an output unit 404 for providing signals to other entities. The input unit 402 and the output unit 404 may be arranged as a single entity or separate entities.

In some embodiments, the input unit 402 may be an interface, bus, and/or communication module for receiving a measured acceleration value from, for example, the acceleration sensor 200 or receiving a measured angular velocity value from the angular velocity sensor 300. In some embodiments, the output unit 404 may be an interface, bus, and/or communication module for outputting or transmitting, for example, an estimated posture quaternion value to the outside.

In addition, the arrangement 400 may comprise at least one readable storage medium 408 in a form of non-volatile or volatile memory, such as an Electrically Erasable Programmable Read-Only Memory (EEPROM), a flash memory, and/or a hard disk driver. The readable storage medium 408 comprises a computer program 410 which includes codes/computer readable instructions that, when executed by the processor 406 in the arrangement 400, cause the hardware arrangement 400 and/or the device (for example, the posture estimation apparatus 100, a mobile terminal etc.) including the hardware arrangement 400 to perform, for example, flows described below in connection with FIG. 1 or 2 and any variations thereof.

The computer program 410 may be configured with computer program codes having, for example, architecture of computer program modules 410A-410C. Therefore, in an exemplary embodiment when the hardware arrangement 400 is used in the posture estimation apparatus 100, the codes in the computer program of the arrangement 400 may comprise a module 410A for calculating an angular velocity control amount at a current moment based on a measured acceleration value and an estimated acceleration value at the current moment; a module 410B for correcting the measured angular velocity value at the current moment according to the calculated angular velocity control amount to obtain the corrected angular velocity value at the current moment; and a module 410C for obtaining an estimated posture quaternion value at a next moment according to the corrected angular velocity value obtained by calculation and an estimated posture quaternion value at the current moment.

The computer program modules may substantially perform the various actions in the flow shown in FIG. 1 or 2 to simulate the posture estimation apparatus 100. In other words, when different computer program modules are executed in the processor 406, they may correspond to different units or modules (for example, the error calculator 1, the proportional-integral-differential controller 2, the angular velocity corrector 3, and/or the posture estimator 4) in the posture estimation apparatus 100.

Although the code means in the embodiments disclosed in conjunction with FIG. 4 are implemented as computer program modules that, when executed in the processor 406, cause the hardware arrangement 400 to perform the actions described below in connection with FIG. 1 or 2, in alternative embodiments, at least one of the code means may be implemented at least in part as a hardware circuit.

The processor may be a single Central Processing Unit (CPU), but may also comprise two or more processing units. For example, the processor may comprise a general purpose microprocessor, an instruction set processor, and/or a related chipset and/or a dedicated microprocessor (for example, an Application Specific Integrated Circuit (ASIC)). The processor may also comprise an on-board memory for caching purposes. The computer program may be carried by a computer program product connected to the processor. The computer program product may comprise a computer-readable medium having stored thereon a computer program. For example, the computer program product may be a flash memory, a Random Access Memory (RAM), a Read Only Memory (ROM), and an EEPROM, and the computer program module may, in an alternative embodiment, be distributed to different computer program products in a form of memory within the device.

The above description is only specific embodiments of the present disclosure, but the protection scope of the present disclosure is not limited thereto. Any changes or substitutions which may easily be reached by those skilled in the art within the technical scope of the present disclosure should be covered within the protection scope of the present disclosure. Therefore, the protection scope of the present disclosure should be determined by the protection scope of the claims.

We claim:

1. A method for estimating a posture estimation method of a three-dimensional target object, comprising:
    calculating an angular velocity control amount at a current moment based on a measured acceleration value and an estimated acceleration value at the current moment;
    correcting a measured angular velocity value at the current moment according to the calculated angular velocity control amount to obtain a corrected angular velocity value at the current moment; and
    obtaining an estimated posture quaternion value at a next moment according to the corrected angular velocity value obtained by calculation and an estimated posture quaternion value at the current moment, so as to estimate a posture of the three-dimensional target object at the next moment;

wherein the calculating the angular velocity control amount at the current moment based on the measured acceleration value and the estimated acceleration value at the current moment further comprises:

calculating an error between the measured acceleration value and the estimated acceleration value at the current moment; and calculating the angular velocity control amount at the current moment by using a proportional-integral-differential control algorithm according to the calculated error;

wherein the calculating the error between the measured acceleration value and the estimated acceleration value at the current moment further comprises:

acquiring the measured acceleration value $a_c$ ($x_c$, $y_c$, $z_c$) at the current moment T;

acquiring the estimated posture quaternion value $Q_T(q_0, q_1, q_2, q_3)$ at the current moment T, and calculating the estimated acceleration value $a_g$ at the current moment T according to the following formula (I):

$$a_g = \begin{bmatrix} 2(q_1q_3 - q_0q_2) \\ q(q_2q_3 + q_0q_1) \\ 1 - 2(q_1^2 + q_2^2) \end{bmatrix}; \text{ and} \quad (I)$$

calculating the error $E_T$ between the measured acceleration value $a_c$ and the estimated acceleration value $a_g$ at the current moment T according to the following formula (II):

$$E_T = a_c \otimes a_g = \begin{bmatrix} y_c \cdot [1 - 2(q_1^2 + q_2^2)] - z_c \cdot 2(q_2q_3 + q_0q_1) \\ z_c \cdot 2(q_1q_3 + q_0q_2) - x_c \cdot [1 - 2(q_1^2 + q_2^2)] \\ x_c \cdot 2(q_2q_3 + q_0q_1) - y_c \cdot 2(q_1q_3 - q_0q_2) \end{bmatrix}. \quad (II)$$

2. The method according to claim 1, wherein the step of calculating the angular velocity control amount at the current moment by using a proportional-integral-differential control algorithm according to the calculated error comprises:

calculating the angular velocity control amount μ at the current moment T according to the following formula (III):

$$\mu = K_p \cdot E_T + K_i \cdot \sum_{n=0}^{T} E(n) + K_d \cdot (E_T - E_{T-1}) \quad (III)$$

where $\sum_{n=0}^{T} E(n)$ represents a discrete integral of the error between the measured acceleration value $a_c$ and the estimated acceleration value $a_g$ from an initial moment 0 to the current moment T; $E_{T-1}$ represents the error between the measured acceleration value $a_c$ and the estimated acceleration value $a_g$ at a last moment T−1; $K_p$ represents a proportional control coefficient; $K_i$ represents an integral control coefficient; and $K_d$ represents a differential control coefficient.

3. The method according to claim 2, wherein the step of obtaining the corrected angular velocity value at the current moment T comprises:

calculating the corrected angular velocity value ω($\omega_x$, $\omega_y$, $\omega_z$) at the current moment T according to the following formula (IV):

$$\omega = \omega_c + \mu \quad (IV)$$

where $\omega_c$ represents the measured angular velocity value at the current moment T.

4. The method according to claim 3, wherein the step of obtaining an estimated posture quaternion value at a next moment comprises:

calculating the estimated posture quaternion value $Q_{T+1}$ ($q_0, q_1, q_2, q_3$) at the next moment T+1 according to the following formula (V):

$$Q_{T+1}(q_0, q_1, q_2, q_3) = \begin{pmatrix} q_0 \\ q_1 \\ q_2 \\ q_3 \end{pmatrix} + \frac{\Delta T}{2} \begin{pmatrix} -\omega_x \cdot q_1 - \omega_y \cdot q_2 - \omega_z \cdot q_3 + \\ \omega_x \cdot q_0 - \omega_y \cdot q_3 + \omega_z \cdot q_2 + \\ \omega_x \cdot q_3 + \omega_y \cdot q_0 - \omega_z \cdot q_1 - \\ \omega_x \cdot q_2 + \omega_y \cdot q_1 \omega_z \cdot q_0 \end{pmatrix} \quad (V)$$

where ΔT represents a sampling time interval of the measured angular velocity value.

5. An apparatus for estimating a posture of a three-dimensional target object, comprising:

a processor; and a memory having instructions stored thereon, which when executed by the processor, cause the processor to:

acquire a measured acceleration value and an estimated acceleration value of the three-dimensional target at a current moment;

calculate an angular velocity control amount at a current moment based on the measured acceleration value and the estimated acceleration value at the current moment;

correct a measured angular velocity value at the current moment according to the calculated angular velocity control amount to obtain a corrected angular velocity value at the current moment; and obtain an estimated posture quaternion value at a next moment according to the corrected angular velocity value obtained by calculation and an estimated posture quaternion value at the current moment, so as to estimate a posture of the three-dimensional target object at the next moment;

wherein the instructions, when executed by the processor, further cause the processor to:

calculate an error between the measured acceleration value and the estimated acceleration value at the current moment; and calculate the angular velocity control amount at the current moment by using a proportional-integral-differential control algorithm according to the calculated error;

acquire the measured acceleration value $a_c$ ($x_c$, $y_c$, $z_c$) at the current moment T;

acquire the estimated posture quaternion value $Q_T(q_0, q_1, q_2, q_3)$ at the current moment T, and calculate the estimated acceleration value $a_g$ at the current moment T according to the following formula (I):

$$a_g = \begin{bmatrix} 2(q_1q_3 - q_0q_2) \\ q(q_2q_3 + q_0q_1) \\ 1 - 2(q_1^2 + q_2^2) \end{bmatrix}; \text{ and} \quad (I)$$

calculate the error $E_T$ between the measured acceleration value $a_c$ and the estimated acceleration value $a_g$ at the current moment T according to the following formula (II):

$$E_T = a_c \otimes a_g = \begin{bmatrix} y_c \cdot [1 - 2(q_1^2 + q_2^2)] - z_c \cdot 2(q_2q_3 + q_0q_1) \\ z_c \cdot 2(q_1q_3 + q_0q_2) - x_c \cdot [1 - 2(q_1^2 + q_2^2)] \\ x_c \cdot 2(q_2q_3 + q_0q_1) - y_c \cdot 2(q_1q_3 - q_0q_2) \end{bmatrix}. \quad (II)$$

6. The apparatus according to claim 5, wherein the instructions, when executed by the processor, further cause the processor to:
calculate the angular velocity control amount µ at the current moment T according to the following formula (III):

$$\mu = K_p \cdot E_T + K_i \cdot \sum_{n=0}^{T} E(n) + K_d \cdot (E_T - E_{T-1}) \quad (III)$$

where $\Sigma_{n=0}^{T} E(n)$ represents a discrete integral of an error between a measured acceleration value $a_c$ and the estimated acceleration value $a_g$ from an initial moment 0 to the current moment T; $E_{T-1}$ represents the error between the measured acceleration value $a_c$ and the estimated acceleration value $a_g$ at a last moment T−1; $K_p$ represents a proportional control coefficient; $K_i$ represents an integral control coefficient; and $K_d$ represents a differential control coefficient.

7. The posture estimation apparatus according to claim 6, wherein the instructions, when executed by the processor, further cause the processor to:
calculate the corrected angular velocity value $\omega(\omega_x, \omega_y, \omega_z)$ at the current moment T according to the following formula (IV):

$$\omega = \omega_c + \mu \quad (IV)$$

where $\omega_c$ represents the measured angular velocity value at the current moment T.

8. The apparatus according to claim 7, wherein the instructions, when executed by the processor, further cause the processor to:
calculate the estimated posture quaternion value $Q_{T+1}(q_0, q_1, q_2, q_3)$ at the next moment T+1 according to the following formula (V):

$$Q_{T+1}(q_0, q_1, q_2, q_3) = \begin{pmatrix} q_0 \\ q_1 \\ q_2 \\ q_3 \end{pmatrix} + \frac{\Delta T}{2} \begin{pmatrix} -\omega_x \cdot q_1 - \omega_y \cdot q_2 - \omega_z \cdot q_3 \\ +\omega_x \cdot q_0 - \omega_y \cdot q_3 + \omega_z \cdot q_2 \\ +\omega_x \cdot q_3 + \omega_y \cdot q_0 - \omega_z \cdot q_1 \\ -\omega_x \cdot q_2 + \omega_y \cdot q_1 + \omega_z \cdot q_0 \end{pmatrix} \quad (V)$$

where $\Delta T$ represents a sampling time interval of the measured angular velocity value.

9. The apparatus according to claim 5, further comprising at least one of:
an accelerometer configured to measure an acceleration of the posture estimation apparatus;
a gyroscope configured to measure an angular velocity of the posture estimation apparatus; or
a magnetometer configured to measure strength of a magnetic field at a position where the posture estimation apparatus is located.

10. The apparatus according to claim 5, wherein the posture estimation apparatus is a mobile terminal or a drone.

11. A non-transitory computer readable storage medium having one or more instructions stored thereon, which when executed by the processor, cause the processor to:
acquire a measured acceleration value and an estimated acceleration value of a three-dimensional target at a current moment;
calculate an angular velocity control amount at a current moment based on the measured acceleration value and the estimated acceleration value at the current moment;
correct a measured angular velocity value at the current moment according to the calculated angular velocity control amount to obtain a corrected angular velocity value at the current moment; and
obtain an estimated posture quaternion value at a next moment according to the corrected angular velocity value obtained by calculation and an estimated posture quaternion value at the current moment, so as to estimate a posture of the three-dimensional target object at the next moment;
wherein the instructions, when executed by the processor, further cause the processor to:
calculate an error between the measured acceleration value and the estimated acceleration value at the current moment; and
calculate the angular velocity control amount at the current moment by using a proportional-integral-differential control algorithm according to the calculated error;
acquire the measured acceleration value $a_c$ ($x_c$, $y_c$, $z_c$) at the current moment T;
acquire the estimated posture quaternion value $Q_T(q_0, q_1, q_2, q_3)$ at the current moment T, and calculate the estimated acceleration value $a_g$ at the current moment T according to the following formula (I):

$$a_g = \begin{bmatrix} 2(q_1q_3 - q_0q_2) \\ q(q_2q_3 + q_0q_1) \\ 1 - 2(q_1^2 + q_2^2) \end{bmatrix} ; \text{ and} \quad (I)$$

calculate the error $E_T$ between the measured acceleration value $a_c$ and the estimated acceleration value $a_g$ at the current moment T according to the following formula (II):

$$E_T = a_c \otimes a_g = \begin{bmatrix} y_c \cdot [1 - 2(q_1^2 + q_2^2)] - z_c \cdot 2(q_2q_3 + q_0q_1) \\ z_c \cdot 2(q_1q_3 + q_0q_2) - x_c \cdot [1 - 2(q_1^2 + q_2^2)] \\ x_c \cdot 2(q_2q_3 + q_0q_1) - y_c \cdot 2(q_1q_3 - q_0q_2) \end{bmatrix}. \quad (II)$$

12. The non-transitory computer readable storage medium according to claim 11, wherein the instructions, when executed by the processor, further cause the processor to:
calculate the angular velocity control amount µ at the current moment T according to the following formula (III):

$$\mu = K_p \cdot E_T + K_i \cdot \sum_{n=0}^{T} E(n) + K_d \cdot (E_T - E_{T-1}) \quad \text{(III)}$$

where $\Sigma_{n=0}^{T} E(n)$ represents a discrete integral of the error between the measured acceleration value $a_c$ and the estimated acceleration value $a_g$ from an initial moment 0 to the current moment T; $E_{T-1}$ represents the error between the measured acceleration value $a_c$ and the estimated acceleration value $a_g$ at a last moment T−1; $K_p$ represents a proportional control coefficient; $K_i$ represents an integral control coefficient; and $K_d$ represents a differential control coefficient.

13. The non-transitory computer readable storage medium according to claim 12, wherein the instructions, when executed by the processor, further cause the processor to:

calculate the corrected angular velocity value $\omega(\omega_x, \omega_y, \omega_z)$ at the current moment T according to the following formula (IV):

$$\omega = \omega_c + \mu \quad \text{(IV)}$$

where $\omega_c$ represents the measured angular velocity value at the current moment T.

14. The non-transitory computer readable storage medium according to claim 13, wherein the instructions, when executed by the processor, further cause the processor to:

calculate the estimated posture quaternion value $Q_{T+1}(q_0, q_1, q_2, q_3)$ at the next moment T+1 according to the following formula (V):

$$Q_{T+1}(q_0, q_1, q_2, q_3) = \begin{pmatrix} q_0 \\ q_1 \\ q_2 \\ q_3 \end{pmatrix} + \frac{\Delta T}{2} \begin{pmatrix} -\omega_x \cdot q_1 - \omega_y \cdot q_2 - \omega_z \cdot q_3 \\ +\omega_x \cdot q_0 - \omega_y \cdot q_3 + \omega_z \cdot q_2 \\ +\omega_x \cdot q_3 + \omega_y \cdot q_0 - \omega_z \cdot q_1 \\ -\omega_x \cdot q_2 + \omega_y \cdot q_1 + \omega_z \cdot q_0 \end{pmatrix} \quad \text{(V)}$$

where $\Delta T$ represents a sampling time interval of the measured angular velocity value.

\* \* \* \* \*